(12) United States Patent
Ohno et al.

(10) Patent No.: US 8,293,955 B2
(45) Date of Patent: Oct. 23, 2012

(54) PRODUCTION PROCESS FOR 1,2,3,4-TETRACHLOROHEXAFLUOROBUTANE AND REFINING PROCESS

(75) Inventors: Hiromoto Ohno, Minato-ku (JP); Toshio Ohi, Minato-ku (JP); Nobutoshi Sasaki, Minato-ku (JP); Kiyoshi Nomura, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 482 days.

(21) Appl. No.: 12/593,831

(22) PCT Filed: Mar. 26, 2008

(86) PCT No.: PCT/JP2008/055756
§ 371 (c)(1),
(2), (4) Date: Sep. 29, 2009

(87) PCT Pub. No.: WO2008/120642
PCT Pub. Date: Oct. 9, 2008

(65) Prior Publication Data
US 2010/0130798 A1 May 27, 2010

(30) Foreign Application Priority Data
Mar. 30, 2007 (JP) .................................. 2007-093946

(51) Int. Cl.
*C07C 17/00* (2006.01)
*C07C 17/38* (2006.01)

(52) U.S. Cl. ........................................ 570/161; 570/178
(58) Field of Classification Search .................. 570/161, 570/178
See application file for complete search history.

(56) References Cited

FOREIGN PATENT DOCUMENTS

| JP | 07-033695 A | 2/1995 |
|---|---|---|
| JP | 2001-247495 A | 9/2001 |
| JP | 2006-342059 A | 12/2006 |

*Primary Examiner* — Jafar Parsa
(74) *Attorney, Agent, or Firm* — Sughrue Mion, PLLC

(57) ABSTRACT

The production process for 1,2,3,4-tetrachlorohexafluorobutane of the present invention is characterized in that 1,2,3,4-tetrachlorobutane is reacted with fluorine in the presence of a solvent containing hydrogen fluoride. The 1,2,3,4-tetrachlorobutane may be obtained by chlorination of 3,4-dichlorobutene-1. Further, the present invention provides as well a process of refining 1,2,3,4-tetrachlorohexafluorobutane obtained in the manner described above. According to the present invention, 1,2,3,4-tetrachlorohexafluorobutane which is useful, for example, as a synthetic raw material for hexafluoro-1,3-butadiene used as an etching gas for semiconductors can industrially efficiently be produced by using 1,2,3,4-tetrachlorobutane which is a by-product of chloroprene and which has so far been disposed.

11 Claims, No Drawings

PRODUCTION PROCESS FOR 1,2,3,4-TETRACHLOROHEXAFLUOROBUTANE AND REFINING PROCESS

FIELD OF THE INVENTION

The present invention relates to a production process for 1,2,3,4-tetrachlorohexafluorobutane and a refining process therefor. More specifically, the present invention relates to a process for producing 1,2,3,4-tetrachlorohexafluorobutane which is useful as a synthetic raw material etc. for hexafluoro-1,3-butadiene attracting attentions as an etching gas etc. for semiconductors and a process of refining 1,2,3,4-tetrachlorohexafluorobutane.

BACKGROUND OF THE INVENTION 1,2,3,4-Tetrachlorohexafluorobutane is a compound which is important as a synthetic raw material etc. for hexafluoro-1,3-butadiene attracting attentions as an etching gas used for fine process of semiconductors. A process described in the following patent document has so far been known as a production process for 1,2,3,4-tetrachlorohexafluorobutane.

A process for producing 1,2,3,4-tetrachlorohexafluorobutane by reacting a compound represented by $CClX^1X^2$—$CClX^3$—$CClX^4$—$CClX^5X^6$ (X is a hydrogen atom or a fluorine atom) with fluorine in a liquid phase is described in Japanese Patent Application Laid-Open No. 2006-342059 (patent document 1). It is described therein that in the above process, a perfluoroalkane, a perfluoroether, a perfluoropolyether, a chlorinated fluorinated hydrocarbon and a perfluoroalkylamine are used as a solvent. The solvent has to be separated from the product, recovered and reused. Also, it is described therein that, when 1,2,3,4-tetrachlorohexafluorobutane is used as a solvent for fluorination reaction, an advantage is obtained that it is unnecessary to separate the solvent from the product, so that it is particularly preferred. However, the fluorination reaction is carried out with low concentrations of the reaction raw materials diluted by the solvent, so that a problem is left in terms of industrially efficiently producing a targeted product.

Further, it is known that optical isomers and a meso form are present in 1,2,3,4-tetrachlorohexafluorobutane, and when various isomers of 1,2,3,4-tetrachlorohexafluorobutane are not distinguished and used as a diluent or a solvent in the form of a mixture, a reaction temperature is set in many cases based on an isomer having a highest melting point among the above isomers. Accordingly, when carrying out a liquid phase reaction, a reaction temperature has to be set at a high temperature to some extent in a certain case in order to carry out the reaction while maintaining a liquid phase. The above manner brings about such a problem that side reactions of producing low boiling fraction and the like by C—C cleavage in fluorination reaction proceed to lower the yield or fluorination goes on in excess.

Further, it is thought as well that provided a product of reaction is used as a solvent, the product is liable to be excessive to the reaction raw material and that reaction of a direction reverse to a direction in which 1,2,3,4-tetrachlorohexafluorobutane is produced is liable to go on in terms of Gibbs's free energy. Accordingly, this allows a problem to be left in the process for producing 1,2,3,4-tetrachlorohexafluorobutane described in the patent document 1 in terms of industrially efficiently producing a targeted product.

Patent document 1: Japanese Patent Application Laid-Open No. 2006-342059

DISCLOSURE OF THE INVENTION

An object of the present invention is to provide a process for industrially efficiently producing 1,2,3,4-tetrachlorohexafluorobutane.

Further, an object of the present invention is to provide a process in which side reactions such as production of low boiling matters and production of excessive fluorides are less liable to be brought about and in which 1,2,3,4-tetrachlorohexafluorobutane can stably be produced.

Further, an object of the present invention is to provide a process of efficiently refining the produced 1,2,3,4-tetrachlorohexafluorobutane.

The present invention relates to the following items [1] to [13].

[1] A production process for 1,2,3,4-tetrachlorohexafluorobutane characterized in that 1,2,3,4-tetrachlorobutane is reacted with fluorine under the presence of a solvent containing hydrogen fluoride.

Further, the embodiments of the above invention described are shown below.

[2] The production process for 1,2,3,4-tetrachlorohexafluorobutane as described in the above item [1], wherein a reaction temperature of the reaction falls in a range of −20° C. to 70° C.

[3] The production process for 1,2,3,4-tetrachlorohexafluorobutane as described in the above item [1], wherein a reaction pressure of the reaction falls in a range of 0.1 MPa to 2.0 MPa.

[4] The production process for 1,2,3,4-tetrachlorohexafluorobutane as described in the above item [1], wherein a concentration of 1,2,3,4-tetrachlorobutane is 10% by mass or more in the solvent containing hydrogen fluoride.

[5] The production process for 1,2,3,4-tetrachlorohexafluorobutane as described in the above item [1], wherein a concentration of hydrogen fluoride contained in the solvent used for reacting 1,2,3,4-tetrachlorobutane with fluorine is 10% by mass or more.

[6] The production process for 1,2,3,4-tetrachlorohexafluorobutane as described in the above item [1], wherein a concentration of the fluorine gas reacted with 1,2,3,4-tetrachlorobutane is 40% by volume or more.

[7] The production process for 1,2,3,4-tetrachlorohexafluorobutane as described in the above item [1], wherein at least a part of 1,2,3,4-tetrachlorobutane is obtained by chlorination of 3,4-dichlorobutene-1.

[8] The production process for 1,2,3,4-tetrachlorohexafluorobutane as described in the above item [7], wherein 1,2,3,4-tetrachlorobutane obtained by the chlorination of 3,4-dichlorobutene-1 described above contains a dl form which is an optical isomer of 1,2,3,4-tetrachlorobutane in an amount of 40% by mass or more.

[9] The production process for 1,2,3,4-tetrachlorohexafluorobutane as described in the above item [1], wherein the solvent contains a chlorocarbon and/or a chlorofluorocarbon.

[10] The production process for 1,2,3,4-tetrachlorohexafluorobutane as described in any of the above items [1] to [9], wherein a reaction liquid containing 1,2,3,4-tetrachlorohexafluorobutane produced by reacting 1,2,3,4-tetrachlorobutane with fluorine in the presence of the solvent containing hydrogen fluoride is introduced into a distillation column to separate at least a part of 1,2,3,4-tetrachlorohexafluorobutane from the reaction liquid; at least a part of the solvent containing hydrogen fluoride from which at least a part of 1,2,3,4-tetrachlorohexafluorobutane has been separated is returned to a reaction apparatus in which 1,2,3,4-tetrachlorobutane is reacted with fluorine to be cyclically used.

[11] A refining process of 1,2,3,4-tetrachlorohexafluorobutane, wherein a reaction liquid containing 1,2,3,4-tetrachlorohexafluorobutane produced by reacting 1,2,3,4-tetrachlorobutane with fluorine in the presence of a solvent containing hydrogen fluoride is introduced into a distillation column to separate at least a part of 1,2,3,4-tetrachlorohexafluorobutane from the reaction liquid; and the separated 1,2,3,4-tetrachlorohexafluorobutane is brought into contact with an alkaline substance and/or water.

[12] The refining process of 1,2,3,4-tetrachlorohexafluorobutane as described in the above item [11], wherein 1,2,3,4-tetrachlorohexafluorobutane contacted with the alkaline substance and/or water is further brought into contact with a porous refining material.

[13] The refining process of 1,2,3,4-tetrachlorohexafluorobutane as described in the above item [12], wherein the porous refining material is zeolite.

That is, the present invention has been made based on the knowledges that 1,2,3,4-tetrachlorobutane is brought into contact with fluorine in the solvent containing hydrogen fluoride in producing 1,2,3,4-tetrachlorohexafluorobutane by using 1,2,3,4-tetrachlorobutane, whereby 1,2,3,4-tetrachlorohexafluorobutane can be produced efficiently and economically and further, that 1,2,3,4-tetrachlorohexafluorobutane thus obtained is separated in at least one distillation column, then brought into contact with alkali and the like and further brought, if necessary, into contact with a porous refining agent, whereby 1,2,3,4-tetrachlorohexafluorobutane can readily be refined.

Advantages of the Invention

According to the present invention, reacting 1,2,3,4-tetrachlorobutane with fluorine in the solvent containing hydrogen fluoride makes it possible to carry out the reaction in a low temperature region. This makes it possible to inhibit generation of low boiling components caused by C—C cleavage in the process of the present invention and further makes it possible to control progress of excessive fluorination reaction or excessive chlorination reaction. Accordingly, the process of the present invention makes it possible to economically, advantageously and industrially produce 1,2,3,4-tetrachlorohexafluorobutane with a high yield and makes side reactions less liable to progress. Therefore, safety of the reaction is high.

PREFERRED EMBODIMENTS OF THE INVENTION

The production process for 1,2,3,4-tetrachlorohexafluorobutane and the refining process thereof of the present invention shall be specifically explained below.

The present invention is a process in which 1,2,3,4-tetrachlorobutane is used as a starting raw material and brought into contact with fluorine in a solvent containing hydrogen fluoride to produce 1,2,3,4-tetrachlorohexafluorobutane.

1,2,3,4-Tetrachlorobutane used as the starting raw material in the present invention is produced, for example, as a by-product in a production stage of chloroprene rubber which is industrially produced, as shown in the chemical formula below. The Formula (1) below represents a principal reaction in producing chloroprene rubber, and Formula (2) represents an example of a side reaction proceeding at the same time as the procession of the reaction shown by Formula (1).

In producing chloroprene rubber, 1,2,3,4-tetrachlorobutane produced by the side reaction shown by Formula (2) has so far been detoxified by burning treatment and the like together with other by-products (chlorides) and disposed.

Chem. 1

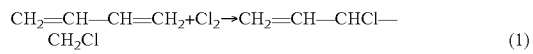

(1)

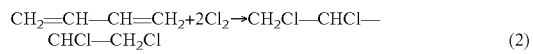

(2)

In the present invention, 1,2,3,4-tetrachlorobutane which is for example produced as a by-product in a production process of chloroprene rubber and disposed as described above is separated and recovered, and it is used as the starting raw material, whereby 1,2,3,4-tetrachlorohexafluorobutane can be produced.

In the present invention, 1,2,3,4-tetrachlorobutane contained in by-products (chlorides) produced in producing chloroprene rubber can be obtained by separating and refining making use of, for example, a distillation column. Use of the distillation column as described above makes it possible to separate 1,2,3,4-tetrachlorobutane into a dl form and a meso form which are optical isomers and recover them.

When 1,2,3,4-tetrachlorobutane obtained in the manner described above is used as a starting raw material, 1,2,3,4-tetrachlorobutane having a purity of usually 95 mole % or more, more preferably 98 mole % or more is used. Use of 1,2,3,4-tetrachlorobutane having, as described above, a high purity as a starting raw material reduces by-products, makes separation thereof easy, enhances a purity of 1,2,3,4-tetrachlorohexafluorobutane obtained and does not require excessive facilities in a refining step, and therefore it is advantageous in terms of production.

As described above, 1,2,3,4-tetrachlorobutane has a dl form which is an optical isomer and a meso form. A melting point (mp) of the dl form which is an optical isomer is 0° C. or lower (boiling point (bp) is about 213° C.), and the dl form is a liquid at room temperature. In contrast with this, a melting point of the meso form is about 73° C. (boiling point is about 213° C.), and the meso form is a white solid at room temperature.

Both dl form and meso form can be separated to some extent by making use of a difference in characteristics between them. In the present invention, a content of the dl form having a lower melting point contained in 1,2,3,4-tetrachlorobutane which is a starting raw material is controlled in a range of usually 40% by mass or more. A content of the meso form falls inevitably in a range of usually 60% by mass or less by controlling an amount of the dl form as described above. Use of 1,2,3,4-tetrachlorobutane containing a dl form and a meso form in such amounts makes it possible to set temperature in dissolving 1,2,3,4-tetrachlorobutane in a reaction solvent and the reaction temperature to lower levels. Therefore, C—C cleavage caused by heating, excessive fluorination reaction and excessive chlorination reaction are less liable to proceed, so that the targeted product can be obtained at a high selectivity and a high yield.

Also, 1,2,3,4-tetrachlorobutane which is the starting raw material in the present invention may be obtained by chlorination reaction of 3,4-dichlorobutene-1 obtained by separation and distillation of a product which is obtained by, for example, chlorinating 1,3-butadiene used in a production stage of chloroprene rubber followed by isomerization reaction.

In production of chloroprene rubber, 3,4-dichlorobutene-1 separated by distillation is used for production of chloroprene rubber through chloroprene obtained by dehydrochlorination reaction. The chlorination reaction of 3,4-dichlorobutene-1 is a side reaction in a production stage of chloroprene rubber, and 1,2,3,4-tetrachlorobutane produced thereby has so far been detoxified by burning and then disposed. In the present invention, 1,2,3,4-tetrachlorohexafluorobutane can be produced by using the 1,2,3,4-tetrachlorobutane, and therefore a disposing facility of 1,2,3,4-tetrachlorobutane is unnecessary. Further, a new industrial use of 1,2,3,4-tetrachlorobutane which has so far been detoxified by burning and then disposed is provided by the present invention, and industrial and economical significances thereof are very large.

As described above, in the production process of the present invention for 1,2,3,4-tetrachlorohexafluorobutane, 1,2,3,4-tetrachlorobutane or 1,2,3,4-tetrachlorobutane produced by chlorination of 3,4-dichlorobutene-1 is used as a starting raw material to carry out fluorination reaction in a reaction solvent.

In general, a pressure proof vessel equipped with a heating and cooling device, a stirrer and a line for blowing gas into a gas phase part or a liquid phase part such as an autoclave can be used as a reactor used in the above reaction.

In the above reaction, a fluorine gas having a high corrosive property is introduced into the reactor, and hydrogen fluoride having a high corrosive property is contained in the reaction solvent. Accordingly, parts brought into contact with the reaction liquid such as the reactor, the stirrer, the line for blowing gas are formed by a material having a corrosion resistance against fluorine, hydrogen fluoride or the like. The examples of the above materials having a corrosion resistance include inconel, hastelloy (HC), SUS and devices obtained by lining them with Teflon (registered trademark). However, nickel which is sometimes contained in corrosive resistant materials is turned into fluoride in a certain case, and the fluoride accelerates substitution reaction of Cl with F. Hence, a material having a low nickel content is preferably used as the corrosive resistant material.

In the present invention, the solvent containing hydrogen fluoride is introduced as a reaction solvent into a pressure proof reactor formed by the corrosive resistant material described above.

The reaction solvent used in the present invention is a solvent containing hydrogen fluoride. A compound which is less liable to be reacted with a fluorine gas and which can maintain a liquid state at the reaction conditions may be contained in the above solvent. A halogenated hydrocarbon is preferable as the above compound. Chlorocarbons and chlorofluorocarbons can be listed as the examples of the above compounds. They can be used alone or in combination. Tetrachloromethane and hexachloroethane can be listed as the examples of the chlorocarbons which can be used as the reaction solvent in the present invention, and trichlorotrifluoroethane and tetrachlorodifluoroethane can be listed as the examples of the chlorofluorocarbons.

On the compounds in which all hydrogen atoms bonded to carbon atoms are substituted with halogen atoms such as a chlorine atom and a fluorine atom, substitution reaction is less liable to proceed if brought into contact with a fluorine gas, and 1,2,3,4-tetrachlorohexafluorobutane which is the targeted compound in the production process of the present invention can be efficiently produced.

Hydrogen fluoride is contained in the reaction solvent described above which is used in the production process of the present invention. Containing hydrogen fluoride in the reaction solvent as described above makes it possible to produce 1,2,3,4-tetrachlorohexafluorobutane from 1,2,3,4-tetrachlorobutane with a high selectivity and a high yield.

In the present invention, an amount of hydrogen fluoride contained in the reaction solvent is usually 10% by mass or more. In the present invention, the amount of hydrogen fluoride in the above reaction solvent preferably falls in a range of 10 to 60% by mass. If the amount of hydrogen fluoride is less than 10% by mass, a reaction rate of the fluorination reaction is reduced to make it difficult to be employed as an industrial process. The fluorination reaction can smoothly be carried out by controlling the amount of hydrogen fluoride in a range of 10 to 60% by mass.

In the present invention, 1,2,3,4-tetrachlorobutane which is the starting raw material is dissolved in the reaction solvent containing hydrogen fluoride as described above.

In dissolving 1,2,3,4-tetrachlorobutane, air in the reaction vessel is substituted with an inert gas such as a nitrogen gas, a helium gas, a neon gas or an argon gas, and then 1,2,3,4-tetrachlorobutane is introduced into the reaction vessel from the line for blowing gas. In this case, 1,2,3,4-tetrachlorobutane is preferably introduced into the reaction device from the line for blowing gas having an introducing port into a liquid phase while stirring the reaction solvent.

1,2,3,4-Tetrachlorobutane is introduced and dissolved in the reaction solvent in the manner described above so that a concentration of 1,2,3,4-tetrachlorobutane in the reaction medium in the reaction vessel falls in a range of usually 10 to 50% by mass. The reaction efficiency is improved by dissolving 1,2,3,4-tetrachlorobutane in the reaction solvent in the amount described above to carry out the fluorination reaction. Further, heating for dissolving the meso form does not have to be carried out even when a content of the meso form in 1,2,3,4-tetrachlorobutane is relatively high, or, if heating is carried out, the heating time is short. Therefore, C—C cleavage in 1,2,3,4-tetrachlorobutane is less liable to be brought about.

After 1,2,3,4-tetrachlorobutane is dissolved in the reaction solvent containing hydrogen fluoride in the manner described above, a fluorine gas is introduced into the reaction vessel from the line for blowing gas to fluorinate 1,2,3,4-tetrachlorobutane.

In this regard, the fluorine gas introduced from the line for blowing gas may be a fluorine gas alone, and usually it is introduced in the form of a diluted mixed gas diluted by the inert gas described above. When the diluted mixed gas is used, a concentration of the fluorine gas contained in the diluted mixed gas is usually 40% by volume or more, and the diluted mixed gas having a concentration falling in a range of 40 to 70% by volume is preferably used. That is, use of the diluted mixed gas having a fluorine concentration of less than 40% by volume results in a slow reaction rate and is industrially disadvantageous. On the other hand, use of the diluted mixed gas having a concentration exceeding 70% by volume makes it difficult to control the reaction, makes C—C cleavage of the raw material liable to be caused and further makes side reaction such as excessive fluorination reaction likely to proceed. Accordingly, in order to industrially produce 1,2,3,4-tetrachlorohexafluorobutane with a higher selectivity and a higher yield, a concentration of the fluorine gas contained in the diluted mixed gas is set preferably in a range of 40 to 70% by volume. The above diluted mixed gas is preferably introduced into the liquid phase from the line for blowing gas.

A reaction temperature in the above fluorination reaction is set in a range of usually −20 to 70° C., preferably 0 to 50° C.

C—C cleavage of 1,2,3,4-tetrachlorobutane, excessive fluorination and excessive chlorination reaction are less likely to be brought about by setting the reaction temperature in the manner described above.

In the temperature range described above, a reaction pressure in the above fluorination reaction is set in a range of usually 0.1 to 2.0 MPa.

An operation of introducing the fluorine gas (diluted mixed gas) described above can be carried out repeating twice or more times. A yield of 1,2,3,4-tetrachlorohexafluorobutane is heightened by repeating.

1,2,3,4-Tetrachlorobutane is fluorinated by carrying out the reaction in the manner described above, and at least a part thereof is converted to 1,2,3,4-tetrachlorohexafluorobutane. A large part of the 1,2,3,4-tetrachlorohexafluorobutane is present dissolved in the reaction solvent, and therefore the reaction solvent, hydrogen fluoride, 1,2,3,4-tetrachlorobutane used as the raw material, 1,2,3,4-tetrachlorohexafluorobutane produced by the reaction and side reaction products are contained in the reaction liquid obtained after carrying out the reaction in the manner described above.

The targeted product in the production process of the present invention is 1,2,3,4-tetrachlorohexafluorobutane, and therefore 1,2,3,4-tetrachlorohexafluorobutane which is the targeted product needs to be separated from the reaction liquid obtained in the manner described above.

A method carried out by distillation using a distillation column is advantageous for separation and refining of the 1,2,3,4-tetrachlorohexafluorobutane. In the refining process of the present invention for 1,2,3,4-tetrachlorohexafluorobutane, at least one distillation column, preferably two or more distillation columns are used to refine 1,2,3,4-tetrachlorohexafluorobutane.

That is, a reaction liquid in a reaction apparatus is introduced into the first distillation column by using an infusion pump or the like to separate low boiling matters and high boiling matters. Since 1,2,3,4-tetrachlorohexafluorobutane which is the targeted product is contained in the low boiling matters, the low boiling matters removed from the first distillation column described above are further introduced, if necessary, into the second distillation column and distilled to remove impurities contained in 1,2,3,4-tetrachlorohexafluorobutane. Further, if necessary, the same operation is repeated in the third and fourth distillation columns.

Hydrogen fluoride, a fluorine gas and the like are mixed in 1,2,3,4-tetrachlorohexafluorobutane thus obtained in a certain case, and therefore 1,2,3,4-tetrachlorohexafluorobutane is brought into contact with an alkaline substance and/or water to transfer water-soluble components such as hydrogen fluoride and a fluorine gas contained in 1,2,3,4-tetrachlorohexafluorobutane into the aqueous phase or to neutralize them.

The examples of the alkaline substances used in the present invention includes alkali metal compounds such as sodium hydroxide, potassium hydroxide and lithium hydroxide and alkaline earth metal compounds such as calcium hydroxide. The above alkaline substances are usually dissolved or dispersed in water to be used.

By bringing the above alkaline substance into contact with 1,2,3,4-tetrachlorohexafluorobutane, acidic components such as hydrogen fluoride and a fluorine gas form salts to move into the aqueous phase. Accordingly, 1,2,3,4-tetrachlorohexafluorobutane can be refined by separating water brought into contact with 1,2,3,4-tetrachlorohexafluorobutane in the above manner. The operation described above can be repeatedly carried out.

When 1,2,3,4-tetrachlorohexafluorobutane is brought into contact with water containing the alkaline substance or water in the manner described above, a part of water is dissolved in 1,2,3,4-tetrachlorohexafluorobutane in a certain case. Therefore, 1,2,3,4-tetrachlorohexafluorobutane brought into contact with water in the manner described above is brought into contact with a porous refining material to remove moisture contained in 1,2,3,4-tetrachlorohexafluorobutane by adsorbing it on the porous refining material.

Carbonaceous solid materials, alumina, zeolite and the like can be listed as the examples of the porous refining materials used in the above case. In the present invention, molecular sieves 3A, 4A and 5A are particularly preferably used. Contact with the above porous refining material can be repeatedly carried out. Temperature in the contact step falls preferably in a range of 10 to 60° C.

A purity of 1,2,3,4-tetrachlorohexafluorobutane refined in the manner described above is usually 98% by mass or more, preferably 99% by mass or more.

A yield of 1,2,3,4-tetrachlorohexafluorobutane based on the starting raw material is usually 60 mole % or more, and 1,2,3,4-tetrachlorohexafluorobutane having a high purity can be very efficiently obtained.

On the other hand, the reaction solvent and the like are contained in the high boiling matters from which 1,2,3,4-tetrachlorohexafluorobutane is separated in the first distillation column in the manner described above, and the above high boiling matters can be used as the reaction solvent in fluorinating 1,2,3,4-tetrachlorobutane and can be cyclically used as well by being returned to the reaction apparatus in which fluorination reaction is carried out. When at least a part of the reaction solvent is cyclically used, the high boiling matters are refined if necessary and can be cyclically used as well.

Since the reaction solvent is not fluorinated by the fluorination reaction described above, cyclic use of at least a part thereof is industrially advantageous.

EXAMPLES

The production process of the present invention for 1,2,3,4-tetrachlorohexafluorobutane and the refining process therefor shall be explained below by showing examples, but the present invention shall not be restricted by them.

<Raw Material Example>

Industrially produced 1,3-butadiene was subjected to chlorination reaction to produce principally 3,4-dichlorobutene-1 and 1,4-dichlorobutene-2. 1,4-Dichlorobutene-2 was converted to 3,4-dichlorobutene-1 by isomerization reaction, and by-products were separated by distillation to obtain 3,4-dichlorobutene-1. The resultant was analyzed by gas chromatography to find that purity of 3,4-dichlorobutene-1 was 99.3 mole %. The 3,4-dichlorobutene-1 was chlorinated by a chlorine gas, and the resulting mixture was separated by distillation to obtain 1,2,3,4-tetrachlorobutane. The resulting was analyzed by gas chromatography to find that purity thereof was 99.1 mole %.

Example 1

20 g of hydrogen fluoride was dissolved in 45 g of tetrachloromethane which was a solvent in a SUS 304-made (Teflon (registered trademark) lining) reactor having a content volume of 200 ml. The reactor was charged with 5 g of 1,2,3,4-tetrachlorobutane obtained in the production example of the raw material described above, and a nitrogen gas was introduced thereinto at a pressure of 1.0 MPa to carry out a leaking test. Then, the nitrogen gas was purged, and the temperature was maintained at 20° C. while stirring.

Then, a 50 volume % fluorine gas diluted with a nitrogen gas was introduced from a liquid phase part through a gas introducing tube installed in the autoclave at a pressure of 0.5

MPa to start reaction. After 2 hours, a gas phase was purged from a gas phase part of the autoclave, and a 50 volume % fluorine gas diluted with a nitrogen was introduced at a pressure of 0.5 MPa and reacted. This was repeated and finally this operation was repeated seven times to finish the reaction. A product containing the solvent was recovered and analyzed by gas chromatography.

The analytical results are shown below.

Yield of 1,2,3,4-tetrachlorohexafluorobutane ($C_4Cl_4F_6$): 74.2%.

The by-products comprised principally pentachloropentafluorobutane ($C_4Cl_5F_5$).

Example 2

10 g of hydrogen fluoride was dissolved in 45 g of tetrachloromethane which was a solvent in the SUS 304-made (Teflon (registered trademark) lining) reactor having a content volume of 200 ml. The reactor was charged with 5 g of 1,2,3,4-tetrachlorobutane obtained in <Raw material example>, and a nitrogen gas was introduced at a pressure of 1.0 MPa to carry out a leaking test. Then, the nitrogen gas was purged, and the temperature was maintained at 20° C. while stirring. Thereafter, the same operation was carried out at the same conditions as in Example 1, and a product containing the solvent was recovered and analyzed by gas chromatography.

The analytical results are shown below.

Yield of 1,2,3,4-tetrachlorohexafluorobutane: 82.1%.

The by-products comprised principally pentachloropentafluorobutane, but a by-produced amount of it was reduced as compared with Example 1.

Example 3

1000 g of hydrogen fluoride was dissolved in 2250 g of tetrachloromethane which was a solvent in a SUS 304-made (Teflon (registered trademark) lining) reactor having a content volume of 10 liter. The reactor was charged with 250 g of 1,2,3,4-tetrachlorobutane obtained in <Raw material example>, and a nitrogen gas was introduced at a pressure of 1.0 MPa to carry out a leaking test. Then, the nitrogen gas was purged, and the temperature was maintained at 20° C. while stirring.

Thereafter, the same operation was carried out at the same conditions as in Example 1, and a product containing the solvent was recovered and analyzed by gas chromatography.

The analytical results are shown below.

Yield of 1,2,3,4-tetrachlorohexafluorobutane: 80.5%.

Then, the product containing the solvent was introduced into a distillation column (theoretical plate number: 25 plates) to separate high boiling matters and low boiling matters. 1,2,3,4-Tetrachlorohexafluorobutane was obtained as a recovered product.

A small amount of hydrogen fluoride was contained in the above recovered product, and therefore it was brought into contact with an aqueous solution of potassium hydroxide followed by dehydration by molecular sieves 4A (manufactured by UNION SHOWA K.K.). A purity of 1,2,3,4-tetrachlorohexafluorobutane was analyzed by gas chromatography to find that the purity was 99.5 mole %.

INDUSTRIAL APPLICABILITY

According to the production process of the present invention for 1,2,3,4-tetrachlorohexafluorobutane, 1,2,3,4-tetrachlorohexafluorobutane which is a raw material of an etching gas for semiconductors can be efficiently produced from 1,2,3,4-tetrachlorobutane which is by-produced in a production process of chloroprene and which has so far been burned and disposed because it has no specific utility value.

In addition, according to the refining process of the present invention of 1,2,3,4-tetrachlorohexafluorobutane, 1,2,3,4-tetrachlorohexafluorobutane having a high purity can be obtained from 1,2,3,4-tetrachlorobutane with a high yield.

Thus, according to the present invention, 1,2,3,4-tetrachlorobutane which has not so far been utilized and has been disposed can be effectively used.

The invention claimed is:

1. A production process for 1,2,3,4-tetrachlorohexafluorobutane characterized in that 1,2,3,4-tetrachlorobutane is reacted with fluorine under the presence of a solvent containing hydrogen fluoride, wherein an amount of hydrogen fluoride in the reaction solvent falls in a range of 10 to 60% by mass and a concentration of 1,2,3,4-tetrachlorobutane in the reaction solvent falls in a range of 10 to 50% by mass.

2. The production process for 1,2,3,4-tetrachlorohexafluorobutane as described in claim 1, wherein a reaction temperature of the reaction falls in a range of −20° C. to 70° C.

3. The production process for 1,2,3,4-tetrachlorohexafluorobutane as described in claim 1, wherein a reaction pressure of the reaction falls in a range of 0.1 MPa to 2.0 MPa.

4. The production process for 1,2,3,4-tetrachlorohexafluorobutane as described in claim 1, wherein a concentration of the fluorine gas reacted with 1,2,3,4-tetrachlorobutane is 40% by volume or more.

5. The production process for 1,2,3,4-tetrachlorohexafluorobutane as described in claim 1, wherein at least a part of 1,2,3,4-tetrachlorobutane is obtained by chlorination of 3,4-dichlorobutene-1.

6. The production process for 1,2,3,4-tetrachlorohexafluorobutane as described in claim 5, wherein 1,2,3,4-tetrachlorobutane obtained by the chlorination of 3,4-dichlorobutene-1 described above contains a dl form which is an optical isomer of 1,2,3,4-tetrachlorobutane in an amount of 40% by mass or more.

7. The production process for 1,2,3,4-tetrachlorohexafluorobutane as described in claim 1, wherein the solvent contains a chlorocarbon and/or a chlorofluorocarbon.

8. The production process for 1,2,3,4-tetrachlorohexafluorobutane as described in any of claims 1 to 7, wherein a reaction liquid containing 1,2,3,4-tetrachlorohexafluorobutane produced by reacting 1,2,3,4-tetrachlorobutane with fluorine in the presence of the solvent containing hydrogen fluoride is introduced into a distillation column to separate at least a part of 1,2,3,4-tetrachlorohexafluorobutane from the reaction liquid; at least a part of the solvent containing hydrogen fluoride from which at least a part of 1,2,3,4-tetrachlorohexafluorobutane has been separated is returned to a reaction apparatus in which 1,2,3,4-tetrachlorobutane is reacted with fluorine to be cyclically used.

9. A refining process of 1,2,3,4-tetrachlorohexafluorobutane, wherein a reaction liquid containing 1,2,3,4-tetrachlorohexafluorobutane produced by reacting 1,2,3,4-tetrachlorobutane with fluorine in the presence of a solvent containing hydrogen fluoride is introduced into a distillation column to separate at least a part of 1,2,3,4-tetrachlorohexafluorobutane from the reaction liquid; and the separated 1,2,3,4-tetrachlorohexafluorobutane is brought into contact with an alkaline substance and/or water.

10. The refining process of 1,2,3,4-tetrachlorohexafluorobutane as described in claim 9, wherein 1,2,3,4-tetrachlorohexafluorobutane contacted with the alkaline substance and/or water is further brought into contact with a porous refining material.

11. The refining process of 1,2,3,4-tetrachlorohexafluorobutane as described in claim 10, wherein the porous refining material is zeolite.

* * * * *